United States Patent
Valentine et al.

[11] Patent Number: 5,453,078
[45] Date of Patent: Sep. 26, 1995

[54] ENDOSCOPIC WEDGE AND ORGAN POSITIONER

[75] Inventors: Douglas R. Valentine, Oakdale, Conn.; John J. Gagliardi, Cranston, R.I.

[73] Assignee: Merocel Corporation, Mystic, Conn.

[21] Appl. No.: 205,799

[22] Filed: Mar. 4, 1994

[51] Int. Cl.$^6$ .................. A61F 2/00; A61M 1/00
[52] U.S. Cl. ......................... 600/37; 604/317
[58] Field of Search ............... 128/897, 856, 128/20; 428/246; 604/15, 151, 158, 164, 285, 317, 358, 367; 606/228; 156/213

[56] References Cited

U.S. PATENT DOCUMENTS

| | | | |
|---|---|---|---|
| 1,562,656 | 11/1925 | Park . | |
| 3,888,248 | 6/1975 | Moore | 128/156 |
| 3,924,627 | 12/1975 | Nystrand | 128/287 |
| 3,932,249 | 1/1976 | Jury et al. | 156/213 |
| 3,961,629 | 1/1976 | Richter et al. | 128/296 |
| 4,019,498 | 4/1977 | Hawtrey et al. | 128/1 R |
| 4,034,759 | 7/1977 | Haerr | 128/260 |
| 4,098,728 | 7/1978 | Rosenblatt | 521/141 |
| 4,159,719 | 7/1979 | Haerr | 128/260 |
| 4,533,356 | 8/1985 | Bengmark et al. | 604/358 |
| 4,553,966 | 11/1985 | Korteweg | 604/317 |
| 4,559,050 | 12/1985 | Iskra | 604/368 |
| 4,565,722 | 1/1986 | Highgate et al. | 428/36 |
| 4,889,107 | 12/1989 | Kaufman | 128/20 |
| 4,979,947 | 12/1990 | Berman | 604/369 |
| 5,074,840 | 12/1991 | Yoon | 604/15 |
| 5,149,332 | 9/1992 | Walton et al. | 604/358 |
| 5,387,206 | 2/1995 | Valentine et al. | 604/358 |
| 5,392,787 | 2/1995 | Yoon | 128/898 |

*Primary Examiner*—Lee S. Cohen
*Assistant Examiner*—Stephen Huang
*Attorney, Agent, or Firm*—Gipple & Hale; John S. Hale

[57] ABSTRACT

An organ securing sponge device comprising a rigid dry absorbent linear compressed sponge body, sheet, net or pouch constructed of sponge material of polyvinyl acetal of a specific pore size density. The sponge when hydrated forming a wedge shaped sponge with a center cut out and an inclined surface which resists movement when engaging an organ, said sponge body when hydrated expands to position an organ which it has been laid adjacent to and having an absorbency of about times its weight.

17 Claims, 2 Drawing Sheets

Fig. 1
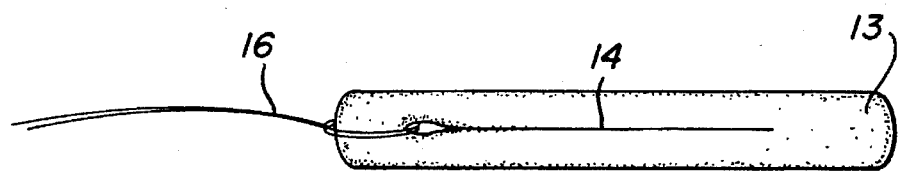
Fig. 2
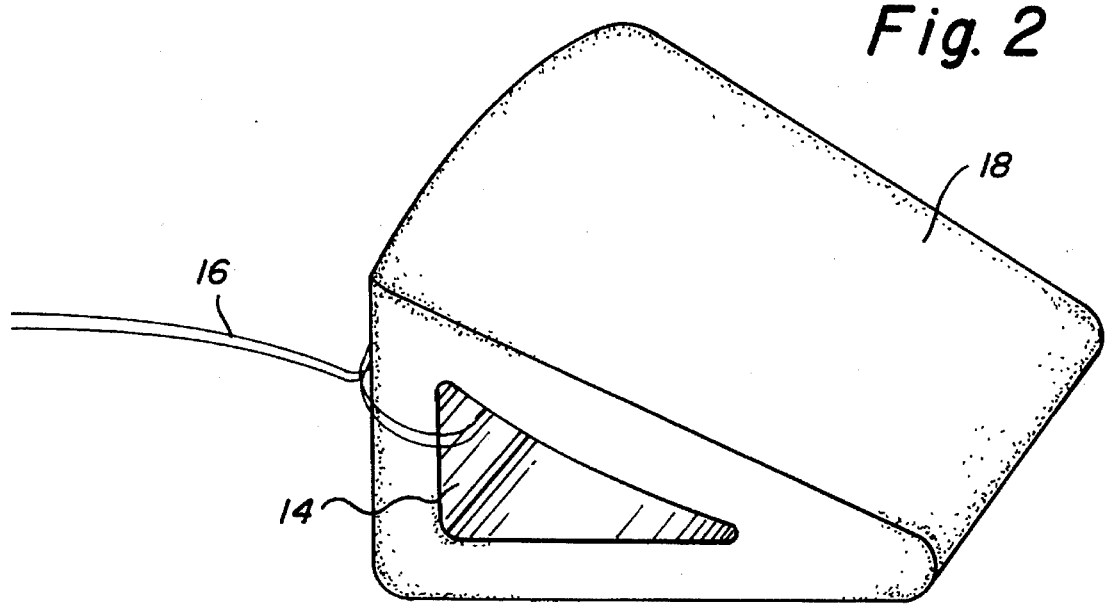
Fig. 3
Fig. 4

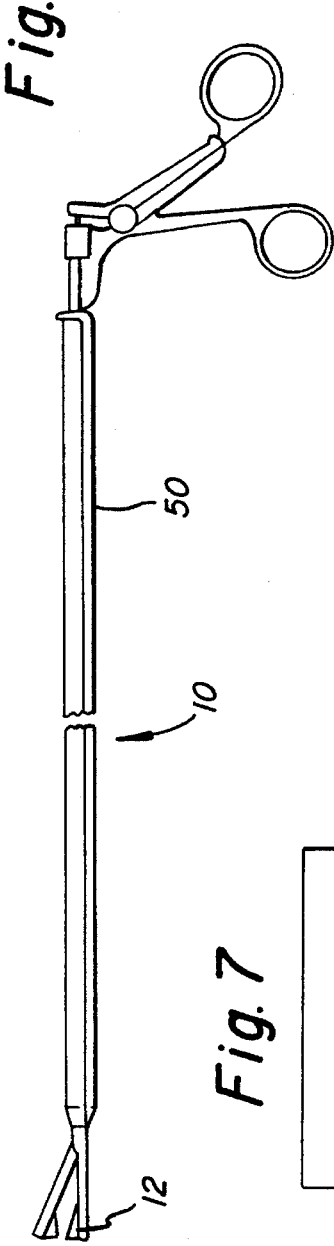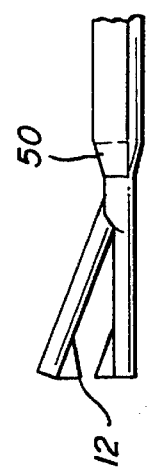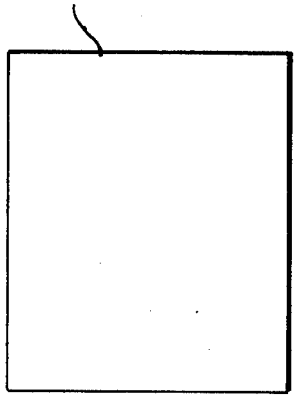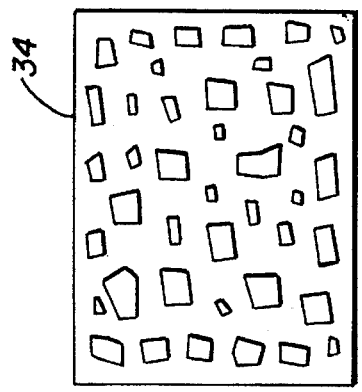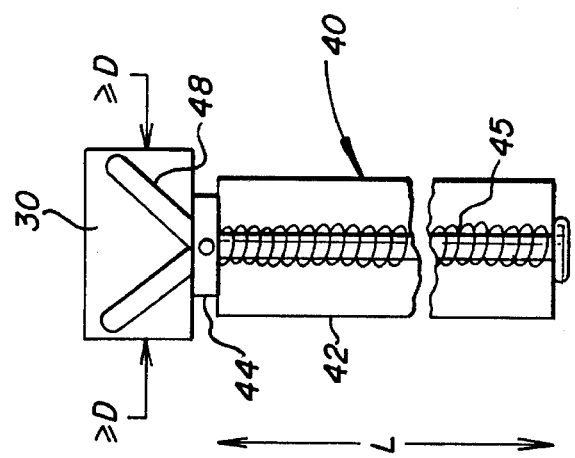

ENDOSCOPIC WEDGE AND ORGAN POSITIONER

BACKGROUND OF THE INVENTION

The present invention generally relates to securing organs within a body cavity and more particularly to securing organs within a body cavity during an endoscopic procedure.

It is often necessary during surgery to displace or temporarily relocate tissue or organs from their natural anatomical position. This is done to facilitate surgery at the site. Organs and tissue must be handled gently to prevent damage or to minimize the tendency to produce adhesions, post operatively.

Securing organs within a body cavity during an endoscopic procedure for diagnostic or therapeutic operations is a continuing problem for the endoscopic physician. Current instruments used to position and manipulate organs within a body cavity such as grasping forceps and retractors have metal, plastic, or rigid composite instrument-to-tissue interfaces that cause tissue trauma during use. Forceps are available with atraumatic jaws, but even these cause noticeable tissue trauma through manipulation of an organ by way of a small grasping area made by a rigid material. A simple, safe and effective endoscopic instrument is needed to secure and position an organ(s) for a particular procedure.

Medical sponges are sometimes used to displace organs or tissues and dam and hold organs and tissues. See for example U.S. Pat. No. 4,533,356 directed toward an absorbent rod shaped device used to keep organs in a given position; U.S. Pat. No. 4,889,107 directed toward a surgical dam constructed of an open celled plastic foam having a metal core allowing it to be bent into a desired configuration and U.S. Pat. No. 3,961,629, a surgical sponge pad having a surfactant coating to accelerate absorption of body fluids into the sponge pads.

A number of patents also show various sponge like devices which have been designed to change shape to provide a desired medical function or to impart a mechanical force for accomplishing a desired result.

In this area, U.S. Pat. No. 5,149,332 discloses an absorbent product which is longitudinally compressed or microcreped to produce microroundulations by compressing the web in its own plane in the direction of its length with compressive forces exerted substantially parallel to a longitudinal direction of the material. The product when compressed has at least 10 microroundulations per inch in the layer in the direction of treatment. The microroundulated layer is shape-retentive and has stored mechanical energy capable under an activating condition such as hydration to cause the product to expand. The product is envisioned to be used as superabsorbent assemblages, menstrual tampons, pads such as bandages, compresses, rolls and the like and liquid distributing articles.

A number of shaped polymeric compositions for surgical use which can absorb liquid and thereby expand or contract in one direction are shown by U.S. Pat. No. 4,565,722. Examples of such different shaped memory devices are shown in the figures of the patent, the even numbers representing expanded devices. One shaped memory device is a triangular shaped endodontic point for insertion into a tooth after a nerve cavity has been removed. The axial length stays unchanged while the product swells radially. Another shaped memory device is initially in the form of a sheath and expands radially for holding severed nerve ends, veins or arteries in close proximity so that the contracted ends of the sheath provide a soft and pliable grip on the nerve, vein or artery ends. Another shaped device is shown which swells in contact with body fluid to a dumbbell shape which can be used for providing a permanent but non-irritant Fallopian tube closure. Still another shaped memory device is directed to a cylindrical blank which expands in diameter. Another shaped memory device expands in thickness only provided that $d_1/d_2$ equals the linear expansion ratio of the material during hydration to give the expanded insert an acurate outer surface for use as a breast implant.

U.S. Pat. No. 4,159,719 discloses a dehydrated wick of tightly coiled cellular sponge like material which when hydrated uncurls and expands radially to snugly engage the inner peripheral wall of the ear canal. Likewise U.S. Pat. No. 4,034,759 discloses a moisture expandable prosthesis constructed of a hollow cylindrical wick of dehydrated regenerated cellulose sponge material. The sponge material is tightly compressed so that it is rigid for insertion endwise into a body opening. When the wick is moistened, it expands radially to engage the inner peripheral walls of the opening and when used in association with an ear canal, provides an axial opening through which the expanded member permits sound waves to reach the ear drum.

U.S. Pat. No. 4,979,947 discloses a resilient foam material collapsed into a small volume condition having a string or cord passing through the material which when introduced into an orifice absorbs moisture to expand at a predetermined size and shape for blockage. Traction on the string during withdrawal results in compression of the contained foam cube allowing comfortable withdrawal from the body orifice.

U.S. Pat. No. 4,019,498 discloses a vaginal device for urinary incontinence in the form of a cellular mushroom-shaped body which is precompressed and inserted in a plastic sleeve. After insertion into the vagina the sleeve is pierced allowing the introduction of air into the sponge-like cells of the device permitting it to expand and exert pressure on the urethra.

It is a general aspect of the invention to provide an organ dam device and an endoscopic instrument incorporating shaped polyvinyl acetal devices to hold, position and secure one or more organs advantageously within a body cavity during an endoscopic procedure.

SUMMARY OF THE INVENTION

The present invention is directed towards a medical organ positioner sponge device used to secure organs within a body cavity. The sponge is compressed into a rigid and dry form and releases mechanical energy through expansion when the device is hydrated. The sponge is constructed of polyvinyl acetal, a material with high absorptive properties and immediate wicking. Upon hydration the sponge material expands resulting in the engaged tissue or organ being engaged and secured.

The organ positioner sponge device can be in the form of a wedge with a cut out or take the form of a sheet or net mounted in a tube assembly.

It is also envisioned that the sponge material can be compressed, rolled, wrapped, corrugated or otherwise folded or compacted to afford introduction into the area where organ positioning is required.

It is an object of the invention that an instrument may be used in connection with the organ positioner sponge device to secure and position the organ(s) for operative work, or alternatively, to secure and/or position the organ(s) outside of the operative area so as to clear an operative area.

It is another object of the invention to provide a hydrated organ positioning sponge device having material which has a soft and forgiving tissue interface which will not abraid or otherwise damage the tissues it contacts as well as providing non-tear single piece removal. The material is also fiber-free causing a fiber-free environment which reduces the development of adhesions, granulomas, infections and embolisms which can be produced by particulate debris.

It is a further object of the invention to absorb moisture and protect the organs. The sponge material absorbs and maintains moisture to prevent the organs it contacts from non-humidified insufflation gas used to create the distended body cavity (i.e., the carbon dioxide commonly used to create a pneumoperitoneum in a laparoscopic procedure). The gases desiccate exposed tissues and the sponge material keeps organs from desicating in the non-humidified environment of the laparoscopic insufflation gases.

It is still another object of the invention to use absorbent sponge material as a suction tip within any endoscopic environment to prevent clogging of the suction tube with large debris, body organisms, etc.

In the accompanying drawings, there is shown an illustrative embodiment of the invention from which these and other of objectives, novel features and advantages will be readily apparent.

BRIEF DESCRIPTION OF THE DRAWINGS

FIG. 1 is a side elevational view of the compressed form of a wedge, shaped organ positioner sponge invention;

FIG. 2 is a perspective view of a wedge shaped sponge invention of FIG. 1 when it is hydrated and expanded;

FIG. 3 is a perspective view of an alternative embodiment of a wedge shaped sponge invention with a curved outer surface;

FIG. 4 is a perspective view of another alternative embodiment of a wedge sponge invention with an undulating outer surface;

FIG. 5 is a perspective view of a endoscopic instrument with absorbent sponge material in a wedge shape configuration for holding, positioning and securing one or more organs within a body cavity during an endoscopic procedure;

FIG. 6 is an enlargement of the jaws of the endoscopic instrument of FIG. 5 showing the wedge shaped sponge device mounted thereon;

FIG. 7 is a top plan view of the a compressed sheet embodiment of the invention;

FIG. 8 is a top plan view of a compressed net embodiment of the invention; and

FIG. 9 is a perspective view of a hollow shaft with spring loaded arms carrying a sponge sheet.

DETAILED DESCRIPTION OF THE DRAWINGS

The preferred embodiment and best mode of the invention is shown in FIGS. 1 and 2. As shown in the FIGS., a wedge shaped sponge 12 with an internal cavity or cut out 14 is compressed to 10 mm in a linear form 13 for trochar cannula insertion. The cut out 14 provided within the body of the wedge serves several purposes. In addition to providing a simple attachment area for the locator string 16, the cut out also lessens product bulk enabling larger wedge sizes to be obtained from a given dry and compressed sponge thickness. Thus, compressed sponges of a sponge thickness of 5, 10, 12, 15 mm can be used. A removal string 16 is held through the cavity 14 and is of a length which is long enough to remain outside the body cavity. The string 16 acts as a tag for location of the wedge and a placement aid if desired and assists in removal of the wedge from the body cavity. The sponge is capable of expanding in a body cavity to form an organ securing mechanism. All wedge edges and corners are soft, rounded and the material is fiber-free and lint free. The sponge material is produced from polyvinyl acetal (PVAc) polymer by the methods described in U.S. Pat. No. 4,098, 728. The sponge material has the describable medical properties of being highly absorbent to liquids, is very soft when wet and also has high wet strength. The polyvinyl acetal material has a controlled pore size uniformly distributed throughout the volume of wedge, the material being fast wicking and having a high liquid holding capacity. The sponge material has an immediate wicking capacity and the capacity to absorb water to the extent of 25 times the sponge weight and a retained holding capacity of 16 times the sponge weight as measured by ASTM D-1117-80. Being soft when wet allows the PVAc sponge to conform to the precise space of the cavity or site or to displace or move the organs and/or tissue without damaging same. Thus, the wedge is useful in placing the organ(s) within the operative site and/or away from the operative site during the procedure. The sponge wedge can be provided with a smooth inclined outer surface 18 as seen in FIG. 2 or have a concave/convex outer surface 19 as seen in FIG. 3. Another wedge configuration is shown in FIG. 4 where the outer surface is formed with a plurality of undulations 20 formed by ridges 22 and valleys 24. These undulations 20 provide greater holding power when engaging an organ. The open pore structure of the MEROCEL CF50 sponge is advantageous as a textured surface to resist movement of the organ. A macro texture can be fabricated onto the slope or incline of the wedge to further resist movement during the surgical procedure.

The PVAc sponge material is produced by Merocel Inc. located in Mystic, Conn. in a variety of pore or cell sizes. These cell sizes can vary from MEROCEL sponge product designation CF 50 which is the preferred embodiment and has a pore size which ranges from about 0.2 mm to about 1.2 mm in diameter. Other sponges with different pore size are CF 100 which has a pore size which ranges from about 0.02 mm to about 0.6 mm in diameter; CF 150 which has a pore size which ranges from about 0.01 mm to about 0.5 mm in diameter; CF 200 which has a pore size which ranges from about 0.004 mm to about 0.4 mm in diameter; and CF 400 which has a pore size which ranges from about 0.004 mm to about 0.2 mm in diameter as determined by Scanning Electron Microscopy at 10x. The aforenoted grade designations CF 50; CF 100; CF 150; CF 200; and CF400 have a respective average pore size of 0.95 mm; 0.45 mm; 0.35 mm; 0.21 mm and 0.19 mm. The present invention preferably uses CF 50 which has a swelling rate which achieve a controlled force against organs and tissue.

The organ placement sponge device 10 is fabricated in the form of a compressed wedge or ramp 11 that hydrates and expands inside the body cavity to form a wedge 12 to position and secure an organ during surgery. The slope of the wedge can be variable to assist in positioning the desired bodily organs into or out of the operative field. If desired, a gully can be formed in the wedge to further assist as a tissue-damming aide. The wedge 12 can also be fabricated in a "C" shape or in other variations providing at least one inclined surface and a resistance to tissue movement. The wedge shape may be designed to be organ and/or application-specific by varying the size, material density, angle of inclination, use of appendages, etc. The PVAc or reinforced PVAc wedge 12 is delivered into the body cavity and generally used to position organs in a number of ways. The most elemental way is by simply hand placing the wedge in the area desired against another tissue or an organ seat to engage the organ to be moved or protected. Another use is with multiple endoscopic wedges used in series or stacked on top of each other. Yet another use is by manipulating the organ placement sponge device wedge via an endoscopic grasping forcep 50 or providing the organ placement sponge device wedge as an attachment to a straight shaft of diameter appropriate for trocar port passage. Alternatively, the organ placement sponge device wedge can be provided as an attachment to an actuating shaft of a diameter appropriate for trocar port passage. The instrument may be used to secure and position the organ for operative work or alternatively to secure and/or position the organ(s) outside of the operative area so as to clear an operative area. The organ placement sponge device can be introduced through a trocar port and into the body cavity in a dry, compressed form. Once in the cavity, the PVAc material is hydrated with the base mounted against tissue, bone or another organ and expanded many times its original size to afford holding, positioning, manipulation, or retraction of organs within the cavity. The organ placement sponge device can be withdrawn at the desired time by pulling the organ placement sponge device with hydrated material through the trocar port.

In another alternative embodiment as shown in FIG. 7, the organ placement sponge device can be fabricated in the form of a compressed sheet 30 which has a thickness ranging from 15 mm to 25 mm that expands for use as a harness to generally hold and position body organs within the body cavity. When the sheet 30, which is preferably constructed of PVAc, is used in combination with the grasping forceps or shafts as previously noted, body organs can be grasped and tensioned as well as positioned, supported, and manipulated. The sheet 30 may be made organ or application-specific by varying the overall dimensions and material density. The use of a macro-void pattern in the material sheet creates a net 34 as seen in FIG. 8. In addition, the sheet or net can be reinforced with a mesh, scrim or suitable higher modulus material to provide additional support. This reinforcement can be embedded within the sponge material or sandwiched between two sheets or portions of sponge material to insure the desired sponge material to tissue interface. The PVAc or reinforced PVAc sheet 30 or net 34 can be delivered into the body cavity and generally used to position organs by one or more endoscopic grasping forceps to create an organ harness, sling, or an adjustable loop or noose. The sheet 30 or net 34 can also be mounted as an attachment to a single actuating assembly 40 that opens into a "Y" once introduced through the port and into the cavity. In the actuating assembly 40, an actuating hollow shaft 42 holds a spring-loaded arm mechanism 44 mounted on rod 45 which releases associated arms 48 open upon entry into the body cavity. A sheet 30 or net 34 having a length of approximately 15 inches and diameter of 0.5 inches is attached to the ends of two pivot arms 48 of the arm mechanism "Y" to hold or cradle an organ. Alternatively, the sheet 30 can be attached to the distal ends of two straight or articulating shafts (not shown). The instrument is packaged with the PVAc material compressed and folded or otherwise compacted to afford introduction through a single trocar port. The sheet 30 or net 34 can also be pre-attached on one end to a single shaft for passage down a first trocar port. A second shaft is provided for passage through a second port located a desirable distance from the first port. The second shaft contains a means such as a clamp for simple and reversible attachment to the free end of the sheet 30 or net 34 inside the body cavity; and the attachment means is released to remove the positioning apparatus from the cavity. Quick and reversible attachment means include mechanical clamping and Velcro.

The organ placement sponge device such as the wedge, sheet and net may be manufactured by cutting the sponge material with an ultrasonic device or other suitable means of cutting known in the art.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. An organ positioning sponge device comprising a rigid dry absorbent sponge body of polyvinyl acetal having an absorbency of at least 16 times its weight formed in a compressed linear form which expands to a wedge shape body defining a cut out when hydrated, said cut out being positioned within said wedge shape body and a removal string secured to said sponge body.

2. An organ positioning sponge device as claimed in claim 1 wherein said wedge shaped body of sponge material has an inclined surface which has a resistance to tissue movement.

3. An organ positioning sponge device as claimed in claim 1 wherein said wedge shaped body of sponge material has an inclined surface which has a concave configuration.

4. An organ positioning sponge device as claimed in claim 1 wherein said wedge shaped body of sponge material has an inclined surface which has a undulating configuration.

5. An organ positioning sponge device as claimed in claim 1 wherein said expanded wedge shaped body has rounded edges and rounded corners.

6. An organ positioning sponge device as claimed in claim 1 wherein said compressed linear form has a thickness ranging from 5 mm to 10 mm.

7. An organ positioning sponge device as claimed in claim 1 wherein said sponge body of polyvinyl acetal is sterile.

8. An organ positioning sponge device as claimed in claim 1 wherein said compressed linear form has a thickness of 12 mm.

9. An organ positioning sponge device as claimed in claim 1 wherein said compressed linear form has a thickness ranging from 5 mm to 12 mm.

10. An organ securing sponge device comprising a rigid dry sterile absorbent sponge body of polyvinyl acetal formed in a sheet of sponge material of a specific pore size ranging from 0.02 mm to 1.2 mm in diameter, said sheet of sponge material being reinforced with another material of a higher modulus to form a sheet of reinforced sponge material, said sheet of reinforced sponge material being collapsed and mounted to expansion means mounted to an actuating shaft with a diameter appropriate for trocar port passages said expansion means also being of a size which allows trocar port passage and constructed to open up said sheet of reinforced sponge material after passage from said trocar port, said sponge body expanding when hydrated and having an absorbency of at least 16 times its weight.

11. An organ securing sponge device comprising a rigid dry absorbent sponge body of polyvinyl acetal formed in sponge material ranging in thickness from 10 to 25 mm having a macro-void pattern formed in said sponge body to create a net with varying throughgoing aperture sizes extending through the sponge material of said sponge body, said net expanding when hydrated.

12. An organ securing sponge device as claimed in claim 11 wherein said net is mounted to a straight shaft of diameter appropriate for trocar port passage.

13. An organ securing sponge device as claimed in claim 11 wherein said net is mounted to an actuating shaft of diameter appropriate for trocar port passage.

14. An organ securing sponge device as claimed in claim 11 wherein said net is sterile.

15. An organ securing sponge assembly comprising a rigid hollow shaft, an arm mechanism retractably mounted within said hollow shaft, spring means engaging said arm mechanism and adapted to extend said arm mechanism outside of said hollow shaft, an absorbent sheet of sponge material attached to said arm mechanism and retractable within said hollow shaft, said sheet being held by said arm mechanism outside of said shaft to provide an organ engaging sheet of material which can be positioned adjacent an organ or portions thereof to provide isolation of an organ or portions thereof, said sponge material expanding when hydrated.

16. An organ securing sponge assembly as claimed in claim 15 wherein said arm mechanism comprises a plurality of arms.

17. An organ securing sponge assembly as claimed in claim 15 wherein said arm mechanism comprises a base member, a plurality of arms moveably connected to said base member, said spring means being mounted to said plurality of arms and adapted to urge said arms away from each other outside of said hollow shaft.

* * * * *